(12) United States Patent
Watanabe et al.

(10) Patent No.: US 11,446,406 B2
(45) Date of Patent: Sep. 20, 2022

(54) PHOTOCATALYTIC DEVICE AND FLUID CLEANING APPARATUS HAVING THE DEVICE

(71) Applicant: APS Japan Co., Ltd., Okasa (JP)

(72) Inventors: Teruo Watanabe, Osaka (JP);
Hidemitsu Watanabe, Osaka (JP);
Hiroyuki Watanabe, Osaka (JP);
Takafumi Watanabe, Osaka (JP);
Masao Yamaguchi, Osaka (JP)

(73) Assignee: APS JAPAN CO., LTD., Osaka (JP)

( * ) Notice: Subject to any disclaimer, the term of this patent is extended or adjusted under 35 U.S.C. 154(b) by 0 days.

(21) Appl. No.: 17/025,104

(22) Filed: Sep. 18, 2020

(65) Prior Publication Data

US 2021/0093745 A1 Apr. 1, 2021

(30) Foreign Application Priority Data

Sep. 20, 2019 (JP) .............................. JP2019-171633

(51) Int. Cl.
*A61L 9/20* (2006.01)
(52) U.S. Cl.
CPC ........... *A61L 9/205* (2013.01); *A61L 2209/12* (2013.01); *A61L 2209/14* (2013.01)
(58) Field of Classification Search
CPC ... A61L 9/205; A61L 2209/12; A61L 2209/14
See application file for complete search history.

(56) References Cited

U.S. PATENT DOCUMENTS 9,963,017 B2 * 5/2018 Kim .................. B60H 1/12

FOREIGN PATENT DOCUMENTS

| JP | 2013-169502 A | 9/2013 |
| JP | 2019-103963 A | 6/2019 |

* cited by examiner

*Primary Examiner* — Timothy C Cleveland
(74) *Attorney, Agent, or Firm* — Kratz, Quintos & Hanson, LLP

(57) ABSTRACT

Provided is a photocatalytic device capable of further enhancing an effect by a photocatalyst and also efficiently dissipating heat emitted from a light applying portion, and capable of further enhancing the purification effect by increase of a light amount. In the photocatalytic device, both end portions of a housing in the lateral direction are in contact with an upper face of a photocatalyst filter to support the photocatalyst filter, and form upper-side edge portions for openings. A center portion of the housing is distant from the photocatalyst filter in an upward direction. Tilted portions are positioned in regions between both the end portions and the center portion. A lower-side inner wall of the housing supports the photocatalyst filter, and forms lower-side edge portions for the openings. A light applying portion is disposed on a lower face of the center portion of the upper-side inner wall.

6 Claims, 18 Drawing Sheets

PHOTOCATALYTIC DEVICE AND FLUID CLEANING APPARATUS HAVING THE DEVICE

BACKGROUND OF THE INVENTION

Field of the Invention

The present invention relates to a photocatalytic device that includes a photocatalyst filter having a photocatalyst carried thereon, and a light applying portion for applying ultraviolet light or visible light to a surface of the photocatalyst filter.

Description of the Background Art

In general, this type of photocatalytic device causes gas to pass through gas holes of the photocatalyst filter, and decomposes and removes, for example, harmful substances or offensive odor in the gas by using a photocatalyst while applying light to the filter surface, to purify the gas (for example, see Patent Literature 1). Such a photocatalytic device has light applying portions in a gas flow path on both surface sides of the photocatalyst filter. Therefore, it is necessary for the light applying portions to be disposed so as not to prevent the flow of gas, so that the light applying portion tends to have a complicated structure as described in, for example, Patent Literature 1. Furthermore, gas passes in the direction perpendicular to the filter surface. Therefore, a distance over which and a time during which gas is in contact with a photocatalyst layer are short, and the purification effect is restricted.

Meanwhile, the applicant of the present invention has already suggested a photocatalytic device in which a photocatalyst filter is a corrugated member, a gas inflow portion and a gas outflow portion are disposed at both end positions of the filter to cause gas to flow along a direction in which ridge portions and trough portions of the filter extend, the top portions of the ridge portions and the bottom portions of the trough portions each have a light passage hole through which ultraviolet light or visible light passes, and a light applying portion for applying ultraviolet light or visible light to the filter surface is provided (see Patent Literature 2). Such a photocatalytic device causes gas to flow on the front and the back surfaces of the ridge portions and the trough portions, from one end side toward the other end side along the direction in which the ridge portions and the trough portions extend. Therefore, a contact area (contact distance and contact time) in which gas and a filter surface are in contact with each other is increased, the effect on purification of gas by a photocatalyst can be substantially enhanced, the light applying portion does not prevent flow of gas, and the photocatalytic device can thus have a simple structure, thereby achieving energy saving and cost reduction. However, heat emitted from the light applying portion is more likely to be accumulated as compared with a conventional device having the light applying portion in a gas flow path.

CITATION LIST

Patent Literature

[PTL 1] Japanese Unexamined Patent Application Publication No. 2013-169502

[PTL 2] Japanese Unexamined Patent Application Publication No. 2019-103963

SUMMARY OF THE INVENTION

Problems to be Solved by Invention

Therefore, the present invention has been made in view of the aforementioned circumstances, and an object of the present invention is to provide a photocatalytic device and a fluid purifying apparatus including the photocatalytic device, in order to solve the problem. According to the photocatalytic device, an effect on purification of fluid by a photocatalyst can be further enhanced, and heat emitted from a light applying portion can be efficiently dissipated. Thus, the purification effect can be further enhanced by increase of a light amount.

The present invention has the following structures.

(1) A photocatalytic device including: a photocatalyst filter including a corrugated member in which a plurality of ridge portions and a plurality of trough portions are respectively formed on an upper side and a lower side of the corrugated member so that each of the ridge portions and each of the trough portions alternate, the photocatalyst filter having, at a top portion of each of the ridge portions, a light passage hole penetrating through the top portion of the ridge portion so that ultraviolet light or visible light passes through the light passage hole, the photocatalyst filter having, on a surface thereof, a photocatalyst carried;

a housing configured to cover an upper side and a lower side of the surface of the photocatalyst filter, the housing having openings as a fluid inflow port or a fluid outflow port, at positions corresponding to opposite end portions of the ridge portions and the trough portions of the photocatalyst filter in a lateral direction along which the ridge portions and the trough portions of the photocatalyst filter extend; and a light applying portion disposed on an upper-side inner wall of the housing which covers the upper face of the photocatalyst filter, the light applying portion being configured to apply ultraviolet light or visible light toward the upper face of the photocatalyst filter, wherein the upper-side inner wall has opposite end portions in the lateral direction, which are in contact with upper faces of opposite end portions, in the lateral direction, of the photocatalyst filter to support the photocatalyst filter, and the opposite end portions of the upper-side inner wall form upper-side edge portions for the openings, the upper-side inner wall has a center portion in the lateral direction, which is positioned with a predetermined distance upwardly from an upper face of a center portion, in the lateral direction, of the photocatalyst filter, tilted portions are positioned in regions between the opposite end portions and the center portion of the upper-side inner wall so that a distance in the upward direction between each of the tilted portions and the upper face of the photocatalyst filter is gradually increased from the opposite end portion sides toward the center portion, a lower-side inner wall of the housing covers the lower face of the photocatalyst filter, is in contact with the lower face of the photocatalyst filter to support the photocatalyst filter, and forms lower-side edge portions for the openings, and the light applying portion is disposed on a lower face of the center portion of the upper-side inner wall.

(2) In the photocatalytic device described in (1), the lower-side inner wall is a flat-plate-like wall, and has, on an upper face, a reflective surface that reflects the light.

(3) In the photocatalytic device described in (1) or (2), reflective surfaces that reflect the light are formed on lower faces of the tilted portions of the upper-side inner wall.

(4) The photocatalytic device described in any one of (1) to (3) in which a plurality of light sources are disposed, as the light applying portion, on the lower face of the center portion of the upper-side inner wall, at predetermined intervals in a longitudinal direction which is orthogonal to the lateral direction, the ridge portions and the trough portions being aligned in the longitudinal direction.

(5) A fluid purifying apparatus including the photocatalytic device described in any one of (1) to (4) incorporated as a unit, in which fluid is caused to pass through a plurality of the units.

The photocatalytic device having the above-described structure according to the present invention includes: both end portions in which the upper-side inner wall of the housing for housing the photocatalyst filter forms the upper-side edge portion of the fluid inflow port or the fluid outflow port for the photocatalyst filter; the center portion distant from the upper face of the center portion of the photocatalyst filter over a predetermined distance in the upward direction; and tilted portions positioned so that a distance in the upward direction between each of the tilted portion and the upper face of the photocatalyst filter is gradually increased from both the end portions toward the center portion. Therefore, flowing fluid passes through the filter in the direction in which the ridge portions and the trough portions extend, moves toward a space on the upper side between the upper-side inner wall and the filter while generating vortexes, returns into the filter, and flows out. Consequently, a distance over which and a time during which fluid and the photocatalyst layer on the filter surface are in contact with each other are increased, thereby enhancing an effect on purification of fluid by the photocatalyst.

The light applying portion is disposed on the lower face side of the center portion of the upper-side inner wall. Therefore, heat emitted from the light applying portion is dissipated directly into fluid moving toward the space between the upper-side inner wall and the filter as described above, and efficiently dissipated into fluid that is in contact with the center portion of the upper-side inner wall on which the light applying portion is disposed, and with the inner wall faces of the tilted portions. Thus, according to the present invention, an effect on purification of fluid by the photocatalyst can be further enhanced, and, simultaneously, heat emitted from the light applying portion can be efficiently dissipated, whereby the purification effect can be further enhanced by increase of a light amount.

Thus, the photocatalytic device according to the present invention has, in itself, a structure for efficiently dissipating heat from the light applying portion into fluid. Therefore, if the photocatalytic device is incorporated as a unit or a plurality of the photocatalytic devices are incorporated as units into an air purifying apparatus, a heat dissipating structure is less likely to be mounted anew for the whole apparatus, and the degree of the freedom in designing can be substantially enhanced.

DESCRIPTION OF THE PREFERRED EMBODIMENTS

Figure 1:
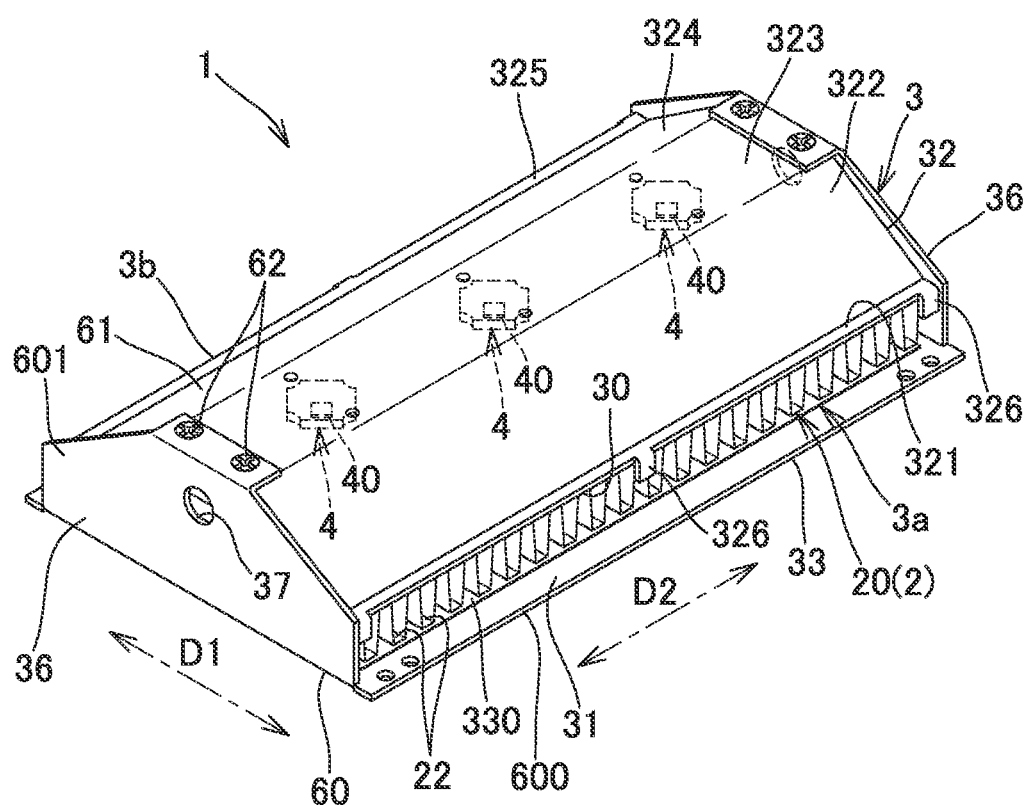
FIG. 1 is a perspective view of a photocatalytic device according to a representative embodiment of the present invention.
Figure 2:
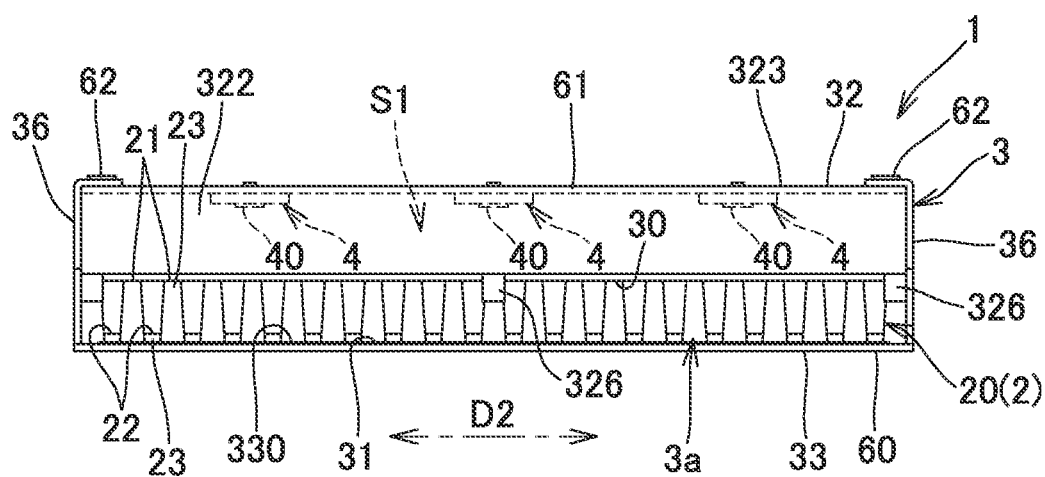
FIG. 2 is a side view of the photocatalytic device.
Figure 3:
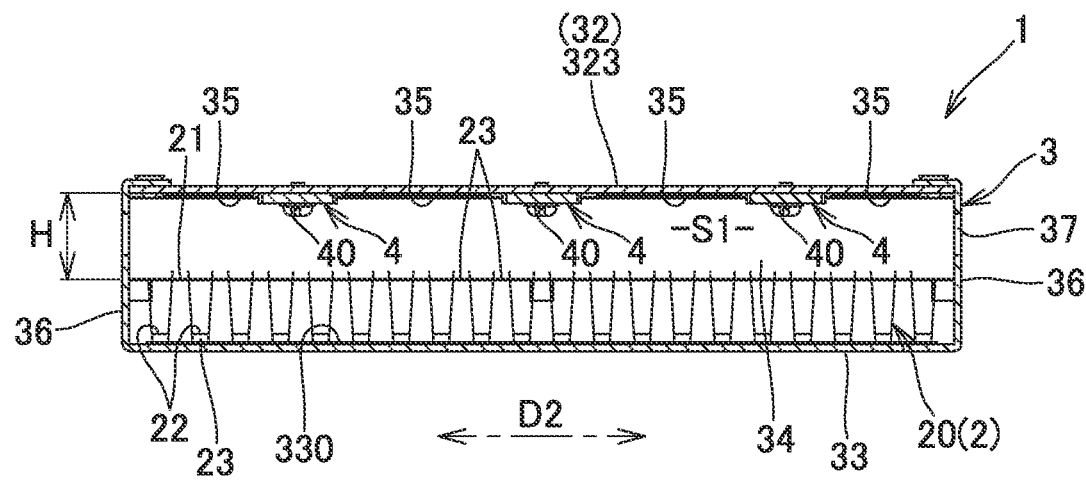
FIG. 3 is a longitudinal cross-sectional view of the photocatalytic device.

Next, embodiments of the present invention will be described in detail with reference to the accompanying drawings.

A photocatalytic device 1 of the present invention includes a photocatalyst filter 2, a housing 3, and light applying portions 4, as shown in FIGS. 1 to 6. The photocatalyst filter 2 includes a corrugated member 20 in which a plurality of ridge portions 21 and a plurality of trough portions 22 are respectively formed on the upper side and the lower side so that the ridge portions 21 and the trough portions 22 alternate. The housing 3 covers the upper and lower faces of the photocatalyst filter 2. The light applying portions 4 are disposed in the housing 3 on the inner face of an upper-side inner wall 32 that covers the upper face of the photocatalyst filter 2, and apply ultraviolet light or visible light toward the upper face of the photocatalyst filter 2.

The photocatalyst filter 2 (corrugated member 20) has light passage holes 23 penetrating through the top portions of the ridge portions 21 and the bottom portions of the trough portions 22 so that ultraviolet light or visible light passes through the light passage holes 23. The photocatalyst filter 2 has a photocatalyst carried on its surface. The light passage hole 23 is a hole through which light passes toward the lower face side of the photocatalyst filter 2. The light passage hole 23 may not necessarily be formed in the bottom portion of the trough portion 22.

Figure 7:
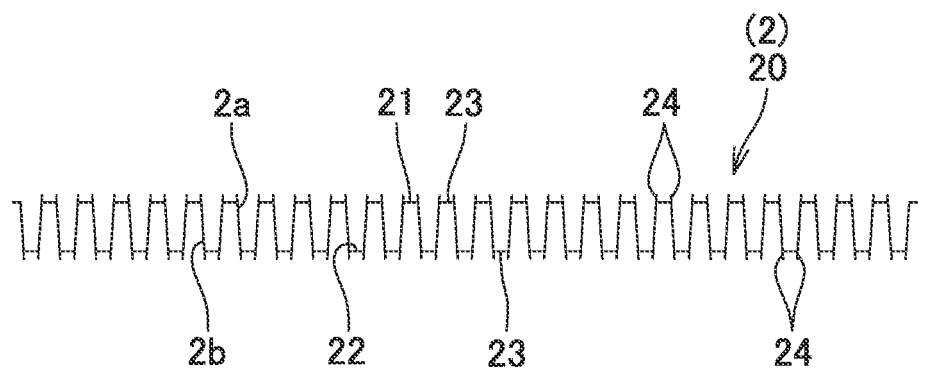
FIG. 7 is a side view of a photocatalyst filter of the photocatalytic device.
Figure 8:
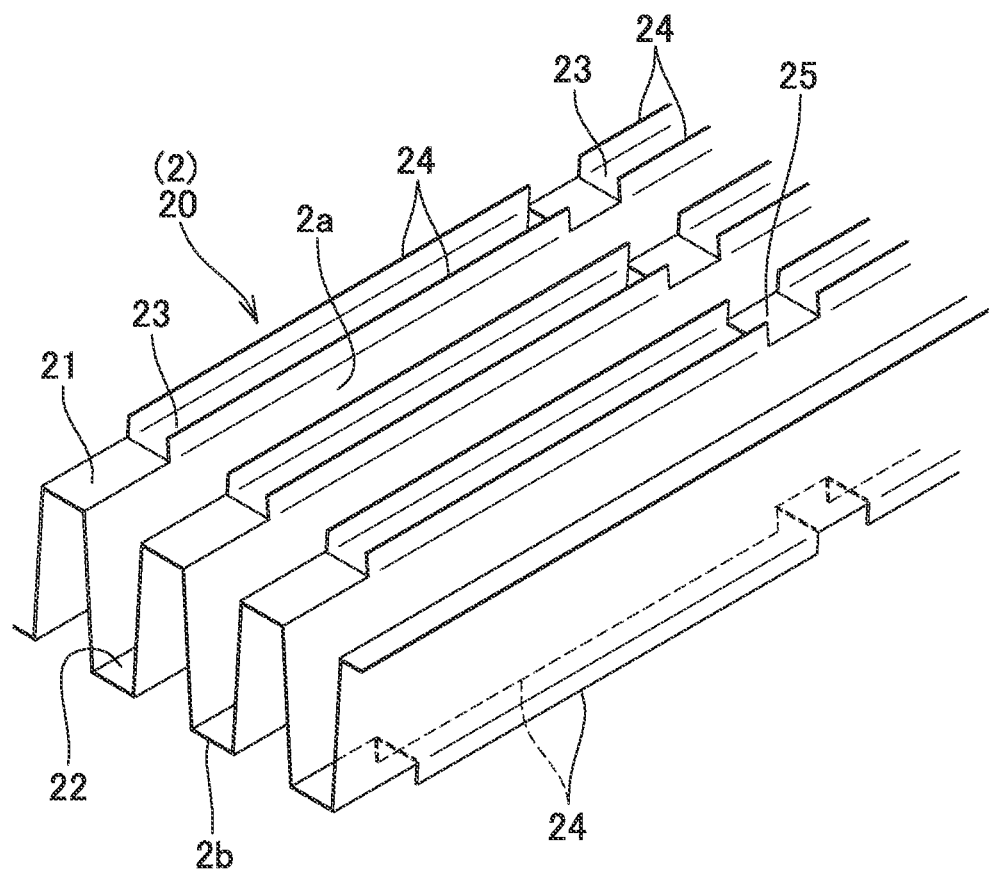
FIG. 8 is a perspective view of a main portion of the photocatalyst filter.

The photocatalyst filter 2 having such a structure is produced in the following manner. That is, a metal plate is pressed and processed into a flat corrugated shape in which all the top portions of the plurality of the ridge portions 21 and all the bottom portions of the plurality of the trough portions 22 are each coplanarly disposed, as shown in FIG. 7 and FIG. 8, and a photocatalyst layer is formed on the surface so as to cover the surface. In the present embodiment, the ridge portions 21 and the trough portions 22 each have a cornered quadrangular shape and form a projecting and recessed corrugated shape as a whole. However, it will be understood that the ridge portions and the trough portions may form a smoothly continuous curved corrugated shape.

Figure 15A:
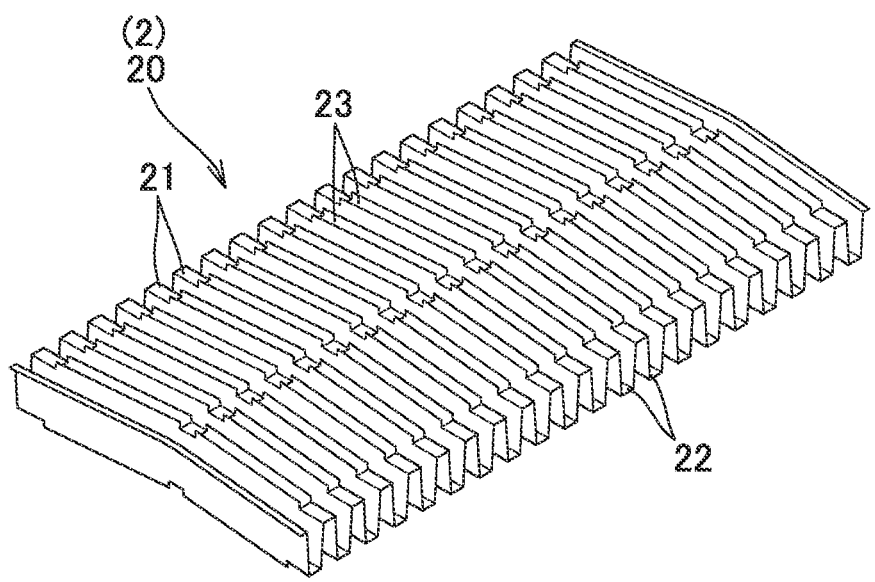
FIG. 15A illustrates a photocatalyst filter according to a modification.
Figure 15B:
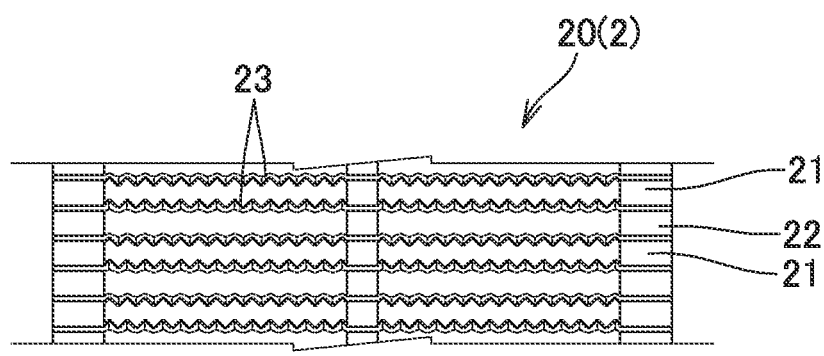
FIG. 15B illustrates a photocatalyst filter according to another modification.
Figure 16:
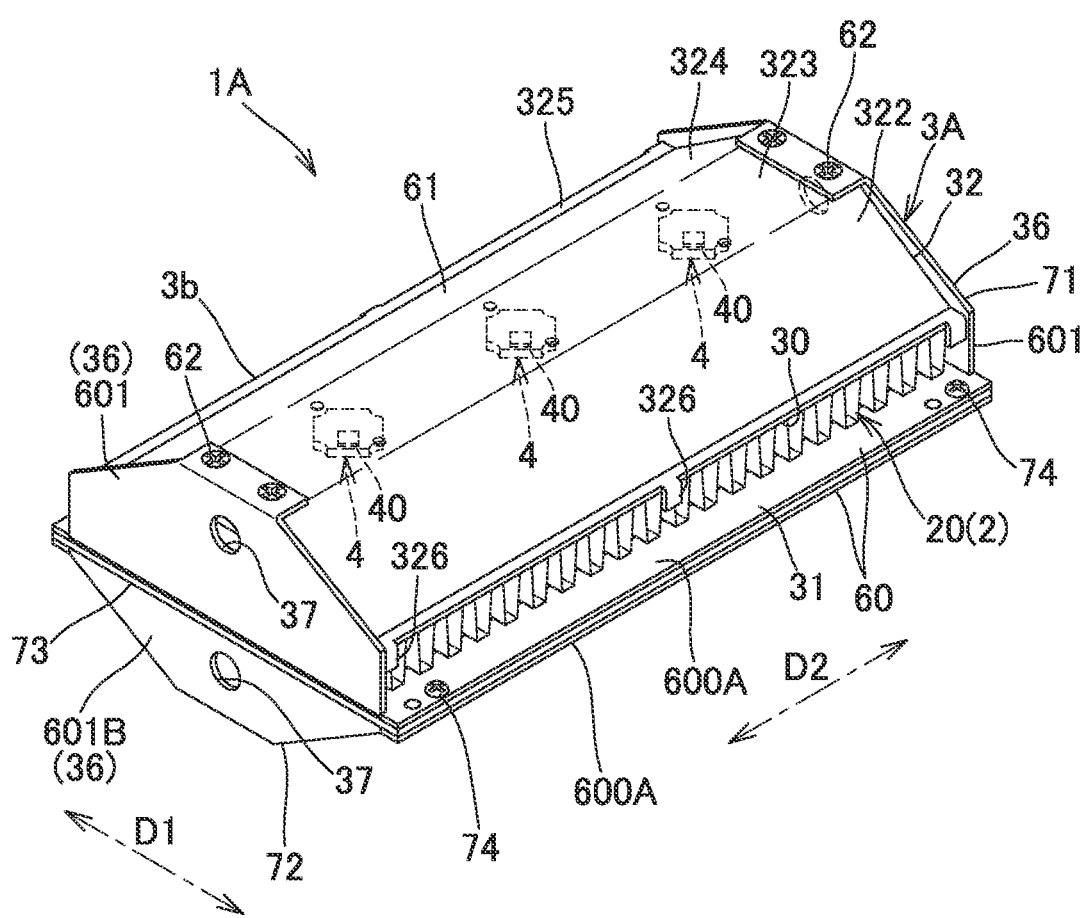
FIG. 16 is a perspective view of a photocatalytic device according to another embodiment of the present invention.
Figure 17:
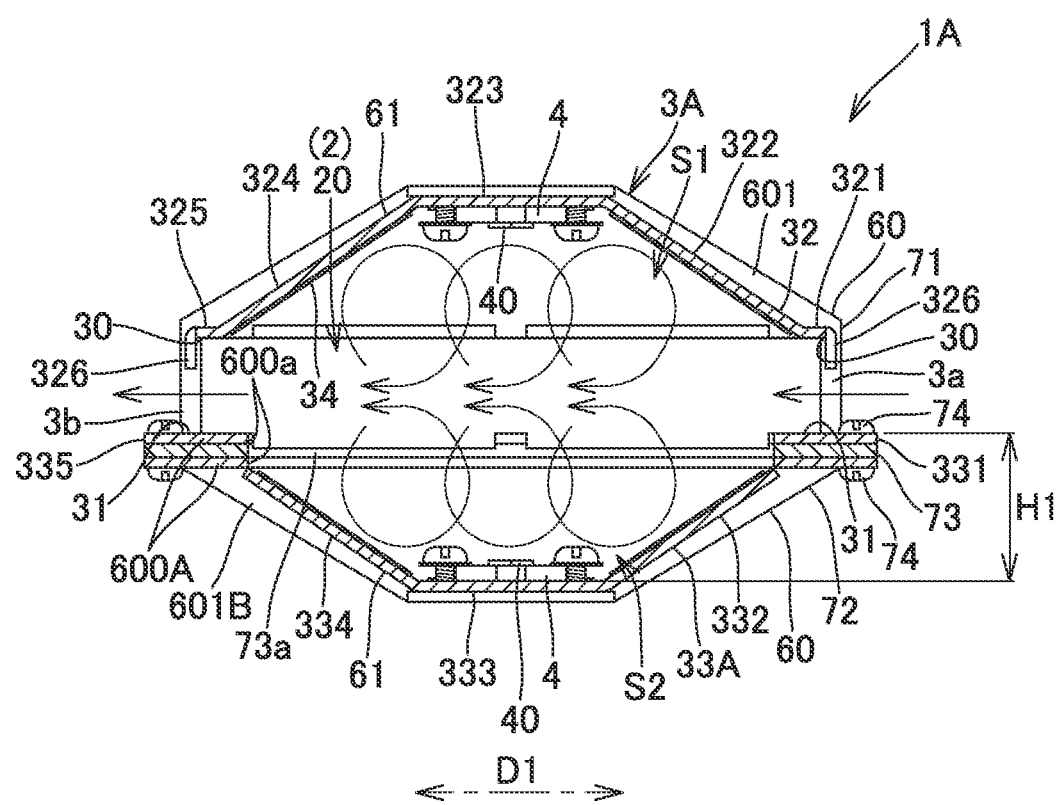
FIG. 17 is a transverse cross-sectional view of the photocatalytic device.
Figure 18:
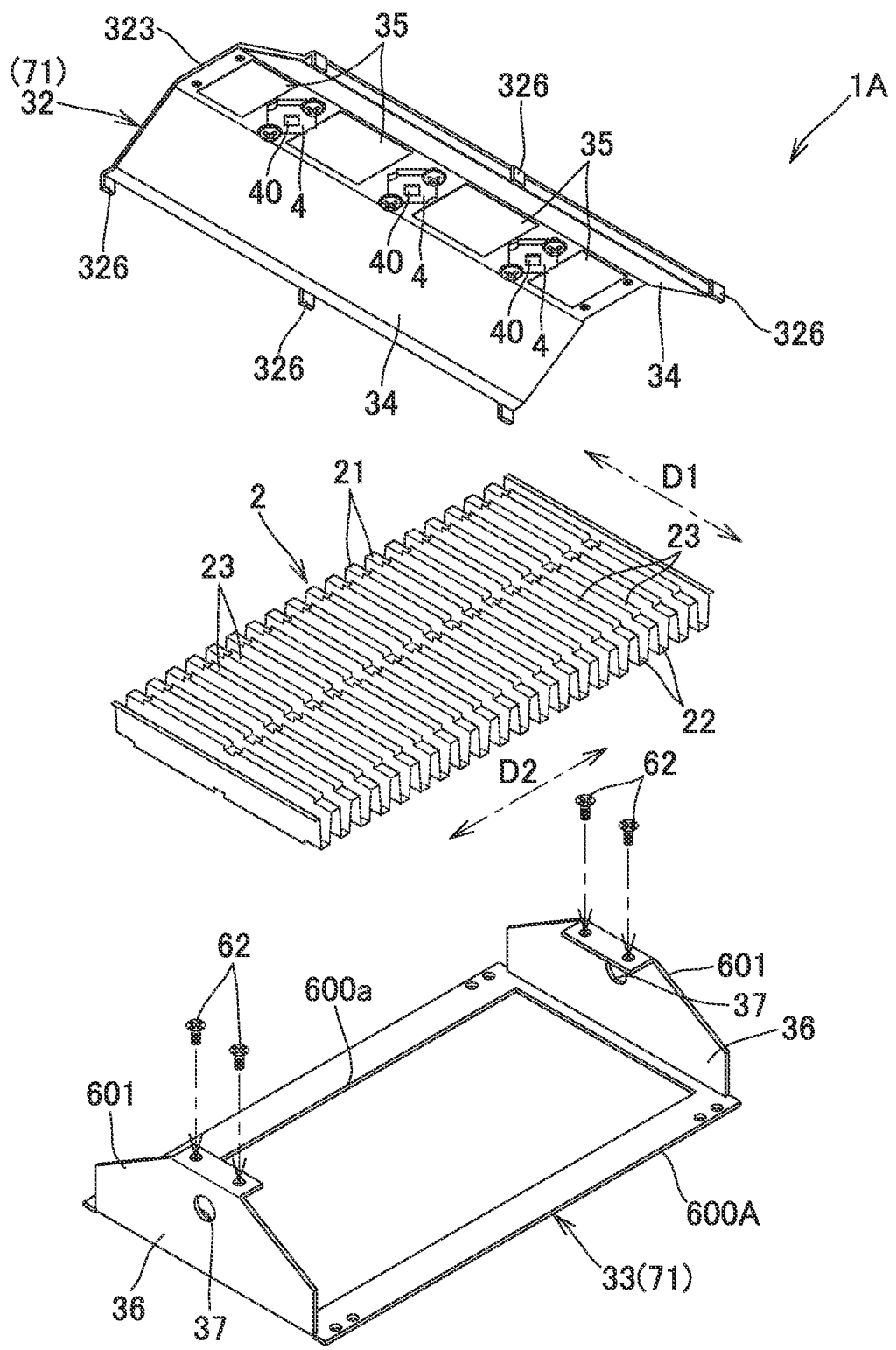
FIG. 18 is an exploded perspective view of a main portion of the photocatalytic device.

The "ridge portion" and the "trough portion" are defined in a manner that a portion projecting toward an upper face side is the ridge portion and a portion projecting toward a lower face side is the trough portion, when one of a recess face and a projection face of the recessed and projecting shape (corrugated shape) is the upper face and the other is the lower face. As the material of the member, various metal materials such as aluminium and stainless steel may be used. However, the material of the member is not limited thereto. The light passage holes 23 may not necessarily be disposed in all of the ridge portions 21 (and the trough portions 22). For example, the light passage holes 23 may be formed so as to skip one or more ridge portions 21. In the present embodiment, the ridge portion 21 and the trough portion 22 linearly extend. However, as shown in FIG. 15A and FIG. 15B, the ridge portion 21 and the trough portion 22 may be formed so as to have a curved shape in a planer view or another shape. Thus, an area in which fluid and light are in contact with each other can be increased, thereby enhancing a photocatalytic effect and a heat dissipating effect described below.

For example, the sizes, the number, and disposition of the light passage holes 23 may be determined as appropriate so as to obtain shape retainability suitable for the usage, the size, and the like of the device of the present invention. In the present embodiment, two light passage holes 23 are consecutively formed with a space on one ridge portion 21 or one through portion 22, as through grooves elongated in the direction in which the ridge portion 21 or the trough portion 22 extends. A bridge portion 25 (remaining portion of the ridge portion 21 or the trough portion 22 between the light passage holes 23) is formed between the two light passage holes 23, and allows shape retainability to be maintained as a whole.

Standing pieces 24 formed by cutting and raising the ridge portion 21 or the trough portion 22 for forming the light passage hole 23, are raised on the projecting face side of the ridge portion 21 or the trough portion 22, on paired opposing opening edge portions, along the longitudinal direction of the light passage hole 23. Thus, in the photocatalyst filter 2 having the standing pieces 24 formed therein, an area in which gas and light are in contact with each other is increased by areas corresponding to the inner face of the light passage hole 23 formed in the ridge portion 21 or the trough portion 22 and the standing pieces 24 on the opening edge portions, so that catalytic reaction (activation of the photocatalyst by light application, and purification of fluid) is efficiently caused. Particularly, the standing pieces 24 in the trough portion function as stilts for raising the lower face of the trough portion 22 from a lower-side inner wall 33, and allows light incidence on the lower face side, flowing of fluid, and photocatalytic reaction to be caused.

The photocatalyst layer is formed by carrying, on the surface of a member, photocatalyst particles such as ultraviolet-excitation-type photocatalyst particles of titanium oxide or the like, and particles of a visible-light-excitation-type photocatalyst that mainly contains tungsten trioxide. A method for carrying the photocatalyst particles (formation of photocatalyst layer) is not particularly limited. However, the method is preferably a slurry dipping method which is relatively low in cost. Other dipping methods, vacuum impregnation, a sol-gel method, and the like may be used.

Figure 4:
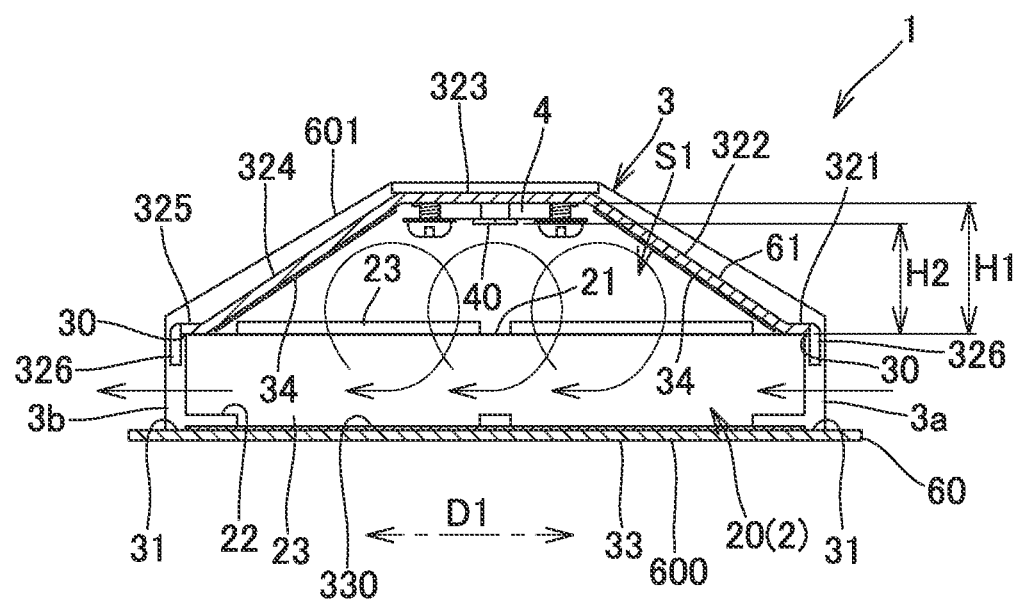
FIG. 4 is a transverse cross-sectional view of the photocatalytic device.

The housing 3 has openings 3a, 3b as a fluid inflow port or a fluid outflow port in positions corresponding to both end portions in a lateral direction D1 in which the ridge portions 21 (and the trough portions 22) of the photocatalyst filter 2 extend, as shown in FIG. 4. Both end portions 321, 325 of the upper-side inner wall 32 of the housing 3 in the lateral direction D1 are in contact with the upper faces of both end portions, in the same direction, of the photocatalyst filter 2 to support the photocatalyst filter 2, and form upper-side edge portions 30 for the openings 3a, 3b. Reference numeral 326 denotes a locking piece for supporting the photocatalyst filter 2 so as to prevent the photocatalyst filter 2 from disengaging from the openings 3a, 3b of the housing 3 in the lateral direction.

Figure 9:
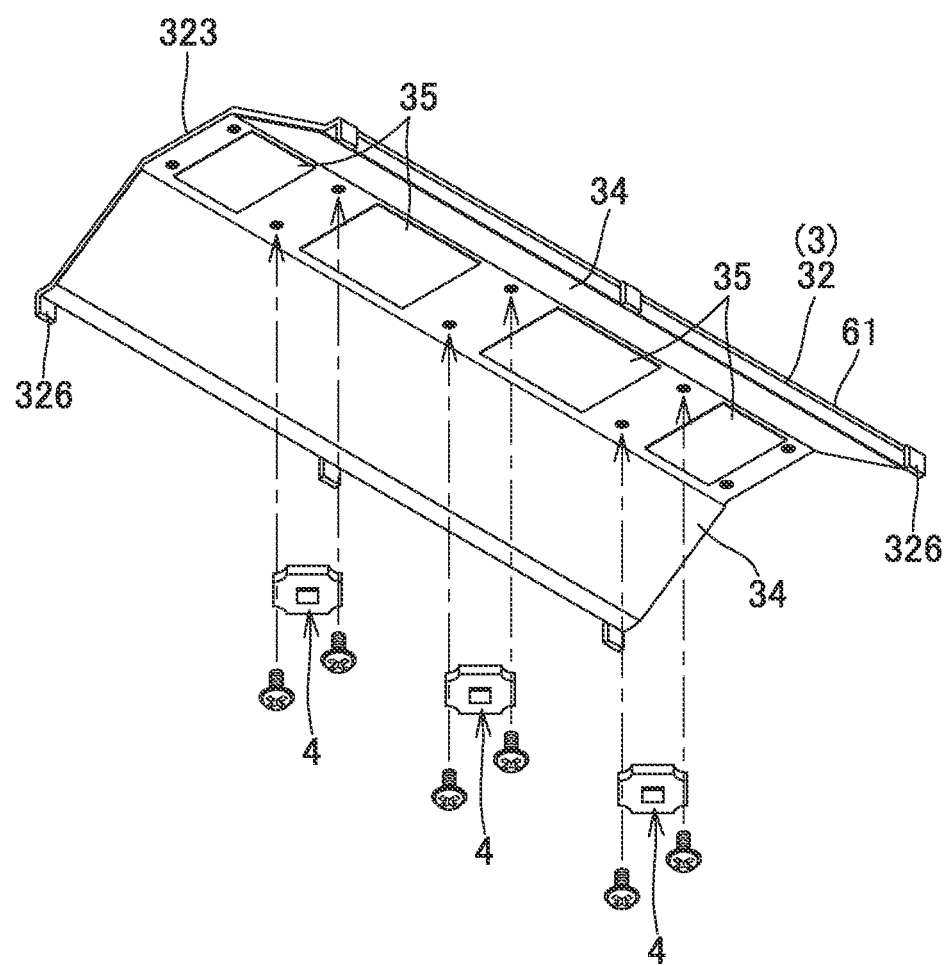
FIG. 9 is an exploded perspective view of an upper-side inner wall and a light applying portion in the photocatalytic device.

A center portion 323 of the upper-side inner wall 32 in the lateral direction D1 is positioned so as to be distant from the upper face of the center portion, in the same direction, of the photocatalyst filter 2 over a predetermined distance H1 in the upward direction. The light applying portion 4 is disposed on the lower face side of the center portion 323. More specifically, in the light applying portion 4, a plurality of light sources 40 are disposed, on the lower face side of the center portion 323 of the upper-side inner wall 32, at predetermined intervals in a direction D2 which is the longitudinal direction orthogonal to the lateral direction D1 and in which the ridge portions and the trough portions are aligned, as shown also in FIGS. 5, 6, and 9.

For the light sources 40, LED elements for emitting ultraviolet light or visible light having a wavelength suitable for the photocatalyst of the photocatalyst filter 2 are preferably used. An optimal distance H2 between the light source 40 and the upper face of the photocatalyst filter 2 depends on a type of the light source 40 (and a lens installed in the light source), and the dimension of the photocatalyst filter 2 in the lateral direction D1. The distance H1 to the center portion 323 of the upper-side inner wall 32 is preferably determined in consideration of the distance H2.

In a region, on the lower face of the center portion 323, other than a portion in which the light applying portions 4 are disposed, a reflective surface 35 is formed to reflect again light reflected by and returned from the photocatalyst filter 2 toward the photocatalyst filter 2. As the reflective surface 35, a metal material face of the housing may be used as it is or the metal material face processed into a mirror surface may be used. In the present embodiment, the reflective surface 35 is formed by adhesion of a mirror surface sheet onto the lower face of the center portion 323.

As shown in FIG. 4, tilted portions 322, 324 are positioned in regions between both the end portions 321, 325 and the center portion 323 of the upper-side inner wall 32. A distance in the upward direction between each of the tilted portions 322, 324 and the upper face of the photocatalyst filter 2 is gradually increased from the both the end portions 321/325 side toward the center portion 323. Thus, a substantially trapezoidal-prism-shaped extra space S1 is formed between the upper-side inner wall 32 and the photocatalyst filter 2. Fluid flowing through the inflow port (opening 3a) into the housing 3 moves in the photocatalyst filter 2 (between the ridge portions and the trough portions) along the lateral direction D1, moves toward the space S1 while generating vortexes, returns into the photocatalyst filter 2, and flows through the outflow port (opening 3b) to the outside of the housing.

Thus, a distance over which and a time during which fluid and the photocatalyst layer on the surface of the photocatalyst filter 2 are in contact with each other can be increased, thereby enhancing the purification effect. Simultaneously, fluid having moved into the space S1 comes into contact with the lower face of the upper-side inner wall 32 (the tilted portions 322, 324, the center portion 323), and heat emitted from the light applying portion 4 is efficiently dissipated through the upper-side inner wall 32 (as a heat sink) into fluid. As the material of the housing 3, various metal materials such as aluminium and stainless steel can be used. However, the material of the housing 3 is not limited thereto, and highly thermally conductive thermoplastic resin exhibiting excellent heat dissipation may also be preferably used.

Figure 10:
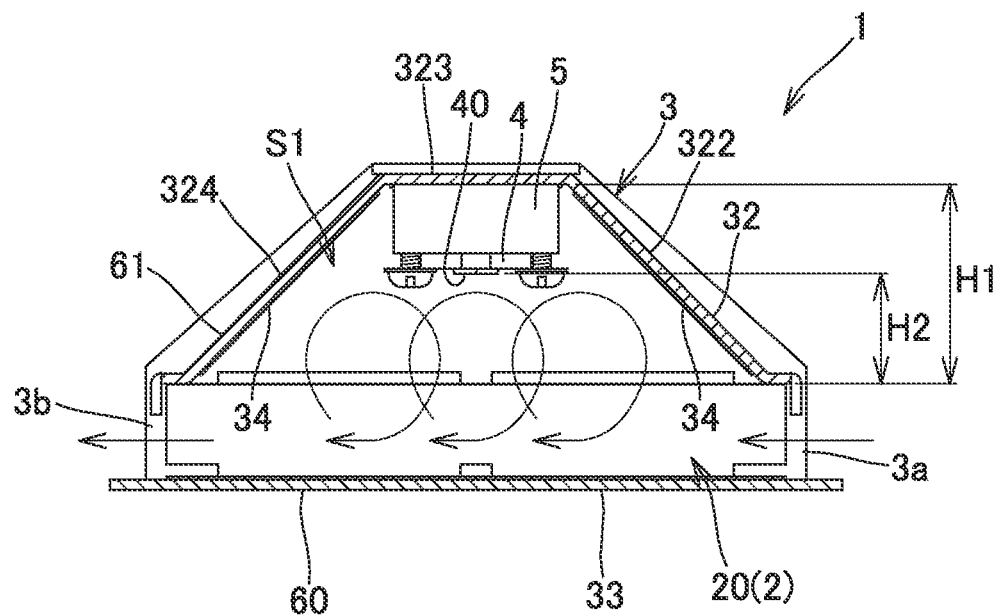
FIG. 10 is a transverse cross-sectional view of a photocatalytic device according to a modification.

Heat from the light applying portion 4 is transmitted also to both the end portions 321, 325 of the upper-side inner wall 32. The heat is dissipated into the fluid and is also transmitted to the photocatalyst filter 2 formed of a metal, and the heat is efficiently exhausted from the surface of the photocatalyst filter 2 into the fluid. Thus, according to the present invention, the upper-side inner wall 32 of the housing 3 and the photocatalyst filter 2 can be caused to efficiently function as a heat sink. FIG. 10 shows a preferable example in which a heat absorbing block 5 formed of an efficient thermally-conductive material such as copper is disposed between the light applying portion 4 and the lower face of the center portion 323 of the upper-side inner wall 32, and heat emitted from the light applying portion 4 is more efficiently transmitted toward the upper-side inner wall 32, whereby heat can be dissipated into fluid. In this case, the height (H1) of the center portion 323 may be increased by the height of the heat absorbing block 5 so that the distance H2 from the light source 40 to the photocatalyst filter 2 is made appropriate.

Figure 11:
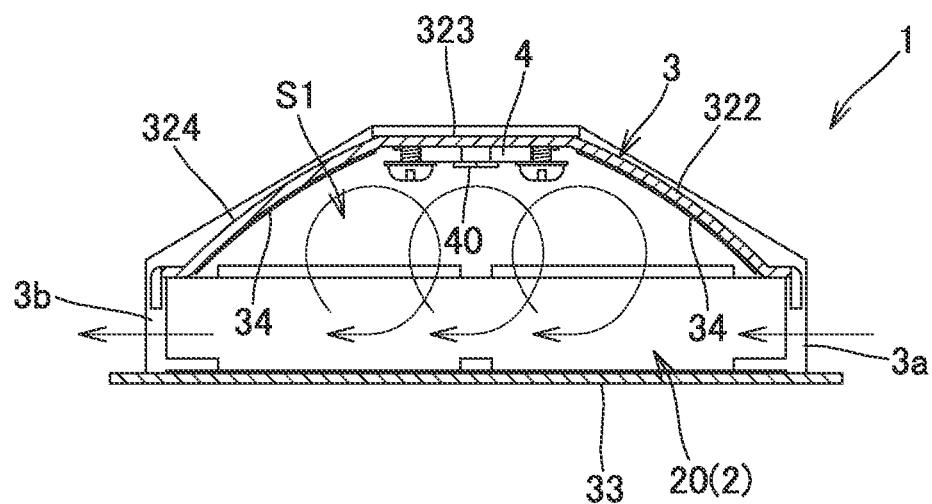
FIG. 11 is a transverse cross-sectional view of a photocatalytic device according to another modification.

Reflective surfaces 34 that reflect light are formed also on the lower faces of the tilted portions 322, 324 of the upper-side inner wall 32. Thus, light emitted from the light applying portion 4 is efficiently reflected toward the photocatalyst filter 2, and light reflected by and returned from the photocatalyst filter 2 is reflected again toward the photocatalyst filter 2. In the present embodiment, the reflective surface 34 is formed by adhesion of a mirror surface sheet similarly to the reflective surface 35. However, a metal material face of the housing may be used as it is, or the metal material face processed into a mirror surface may be used. The tilted portions 322, 324 are flat plate-like walls in the present embodiment. However, it will be understood that, as shown in FIG. 11, the tilted portions 322, 324 may be walls each having a curved surface.

Figure 5:
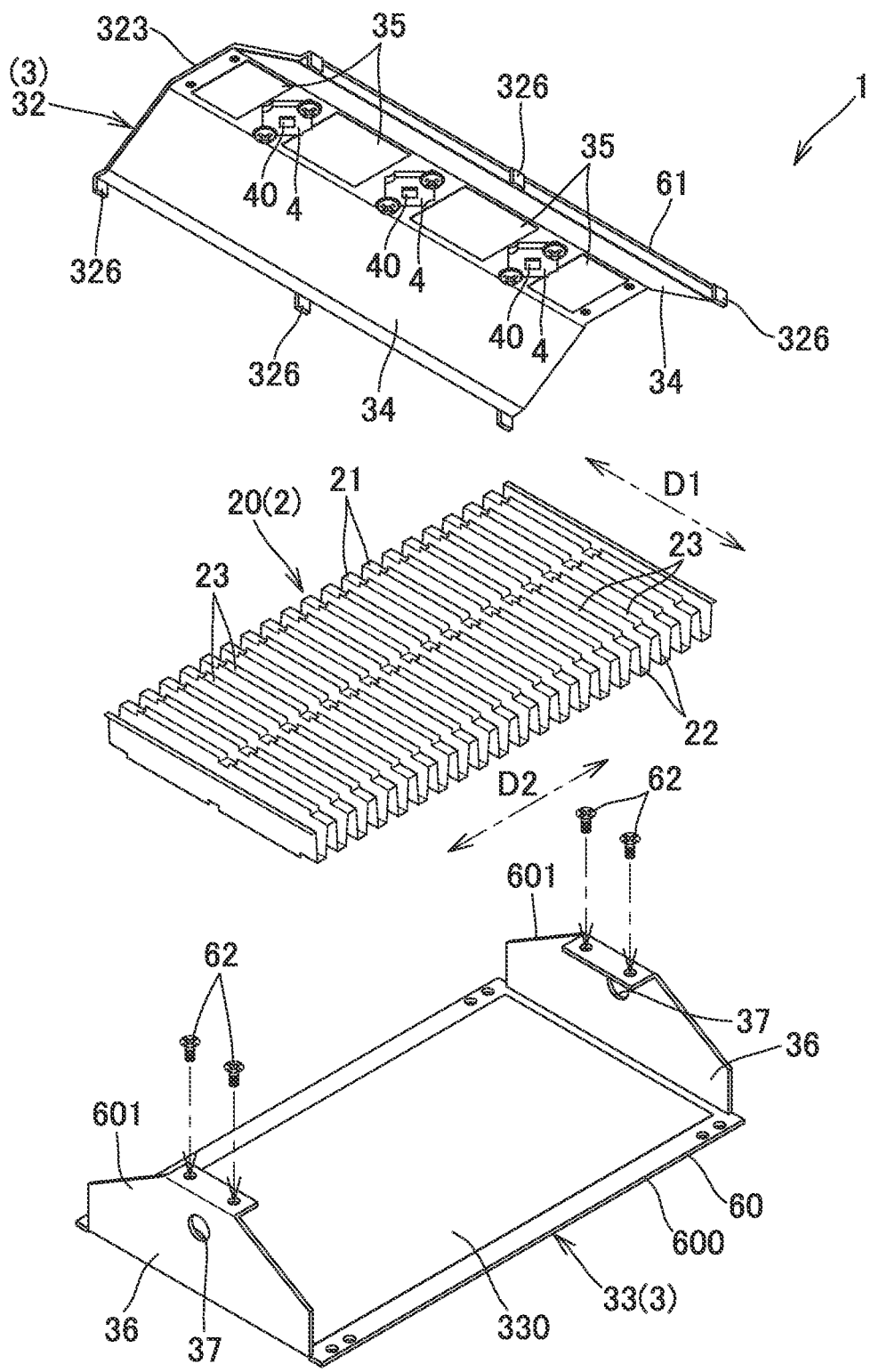
FIG. 5 is an exploded perspective view of the photocatalytic device.
Figure 6:
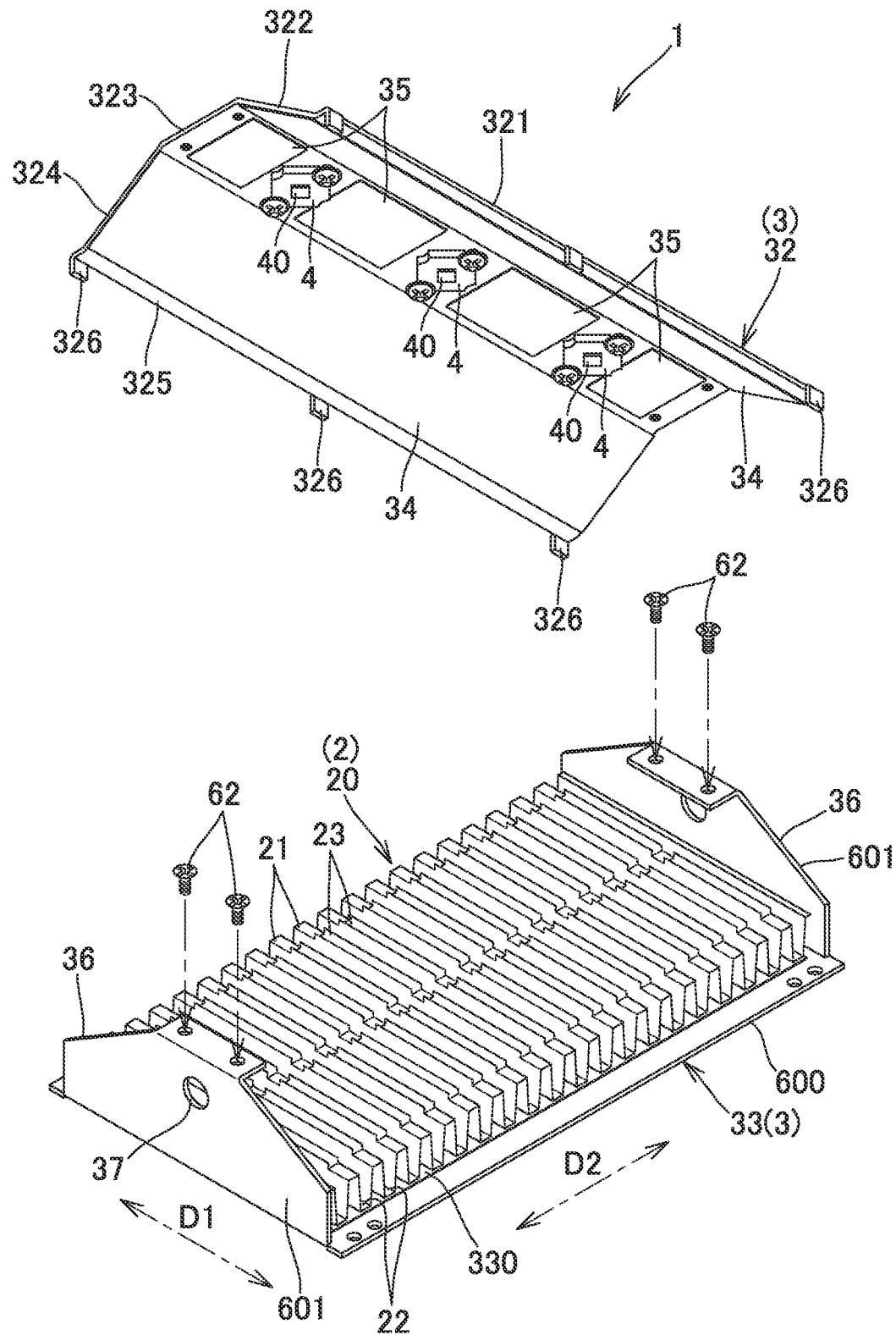
FIG. 6 is an exploded perspective view of the photocatalytic device.

In the housing 3, the lower-side inner wall 33 that covers the lower face of the photocatalyst filter 2 is a flat-plate-like wall that is in contact with the lower face of the photocatalyst filter 2 to support the photocatalyst filter 2, and forms lower-side edge portions 31 for the openings 3a, 3b. As shown in FIG. 5, a reflective surface 330 that reflects light emitted from the light applying portion 4 is formed on the upper face of the lower-side inner wall 33. In the present embodiment, the reflective surface 330 is formed by adhesion of a mirror surface sheet similarly to the reflective surfaces 34, 35. However, a metal material face of the housing may be used as it is, or the metal material face processed into a mirror surface may be used.

Light applied toward the upper face of the photocatalyst filter 2 by the light applying portion 4 activates the photocatalyst on the surface, passes through the light passage holes 23 of the ridge portions 21 and the trough portions 22 of the filter 2 toward the lower surface side, and is reflected by the reflective surface 330 of the lower-side inner wall 33. Thus, the light is applied to the entirety of the lower face of the photocatalyst filter 2, and the photocatalyst carried on the lower face is similarly activated to purify fluid that is in contact with the photocatalyst.

A fan for forcing fluid to flow into/out of the housing may be disposed in the opening 3a side or 3b side. Reference numeral "36" denotes side walls that close both ends of the housing 3 in the longitudinal direction, and are formed as hexagonal walls that close the trapezoidal space S1 and both ends of the photocatalyst filter 2 in the longitudinal direction. Reference numeral "37" denotes a wiring hole formed in the side wall and allows passage of wiring for supplying power to the light sources 40 of the light applying portion 4. The interior of the housing 3 is substantially enclosed except for such a wiring hole and the fluid inflow port and the fluid outflow port (openings 3a, 3b), and fluid having moved into the space S1 is returned toward the photocatalyst filter 2 and flows out while being purified by catalytic action. In the present embodiment, the housing 3 has a divisional structure that includes a base portion 60 and a lid portion 61. The base portion 60 includes a base plate 600 that forms the lower-side inner wall 33 having the flat-plate-like shape as described above, and hexagonal side plates 601 that form the side walls 36 standing on both ends in the longitudinal direction. The lid portion 61 forms the upper-side inner wall 32 that has the substantially open-ended triangular cross-sectional shape as described above and is fixed to the upper end portions of the side plates 601 of the base portion 60 by mounting screws 62. However, the housing 3 of the present invention is not limited to such a structure in any way.

Figure 12:
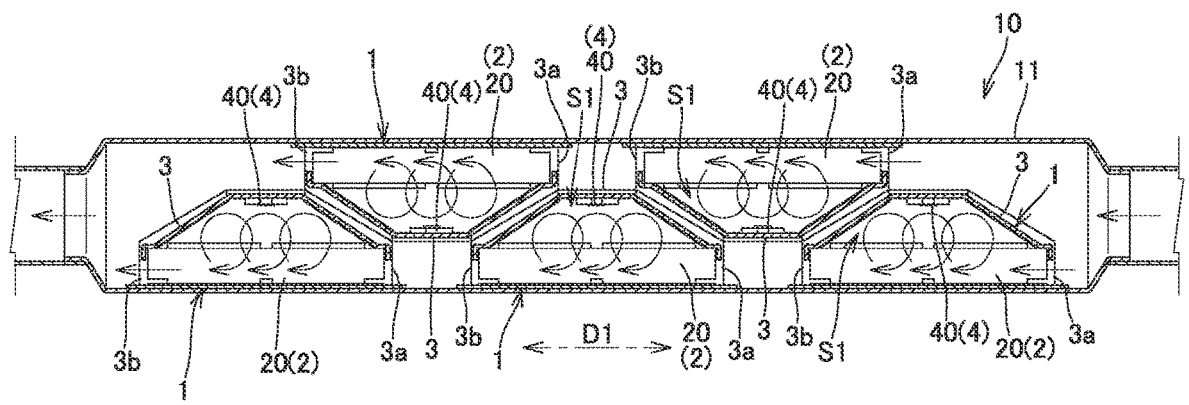
FIG. 12 is a cross-sectional view of a fluid purifying apparatus having a plurality of the photocatalytic devices incorporated therein.
Figure 13A:
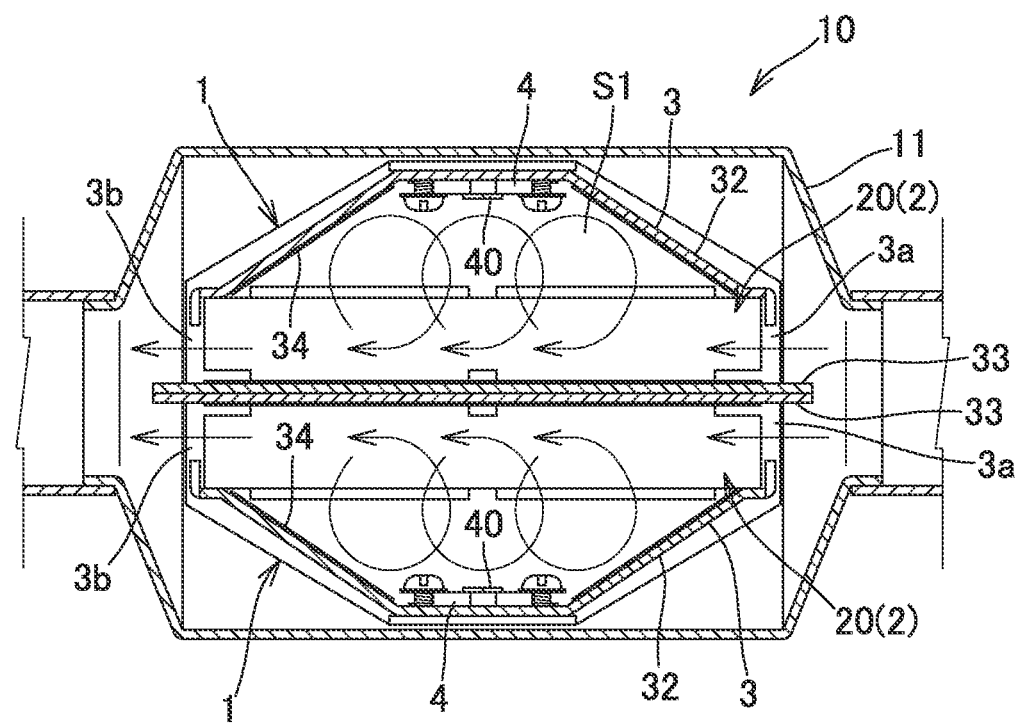
FIG. 13A is a transverse cross-sectional view of another example of the fluid purifying apparatus.
Figure 13B:
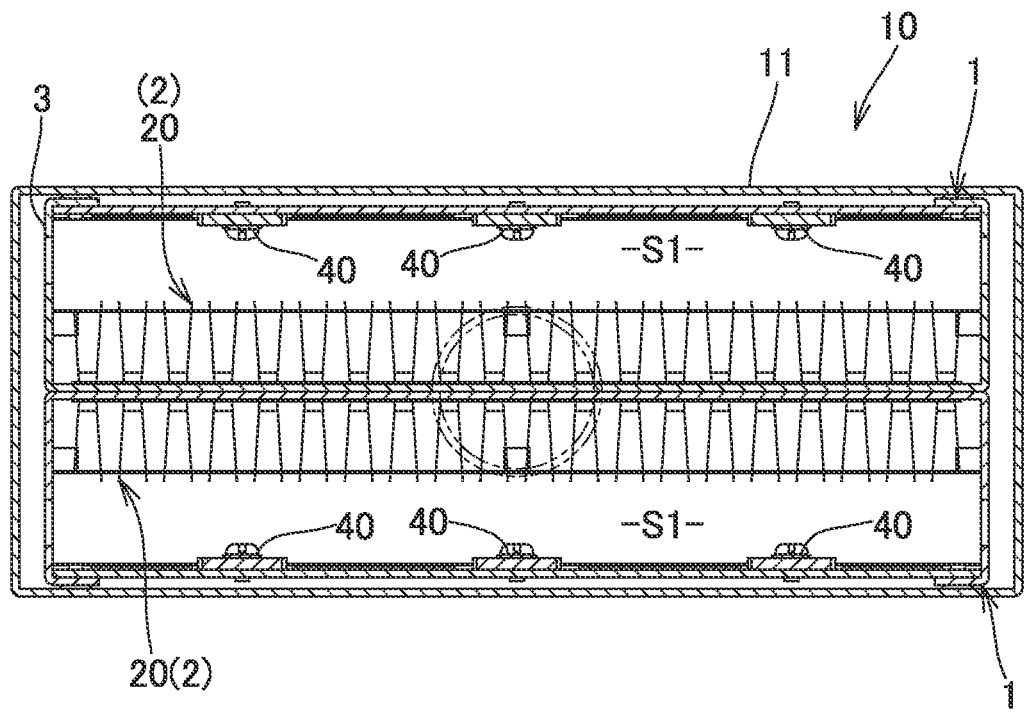
FIG. 13B is a longitudinal cross-sectional view of another example of the fluid purifying apparatus.

FIG. 12 shows an embodiment in which a plurality of the photocatalytic devices 1 according to the present embodiment are incorporated as units into a housing 11 of an air purifying apparatus 10. Each unit (photocatalytic device 1) has, in itself, a structure for efficiently dissipating, into fluid, heat from the light applying portion 4 disposed thereinside, so that a heat dissipating structure need not be mounted to the apparatus 10 anew. FIG. 13A and FIG. 13B show another example of the air purifying apparatus 10. As in this example, in a case where the air purifying apparatus 10 is structured such that the photocatalytic devices 1 are combined with each other by the lower side portions of the housings 3 of the photocatalytic devices 1 being joined to each other, and stored in the housing 11, fluid can be efficiently supplied to each photocatalytic device 1.

Figure 14:
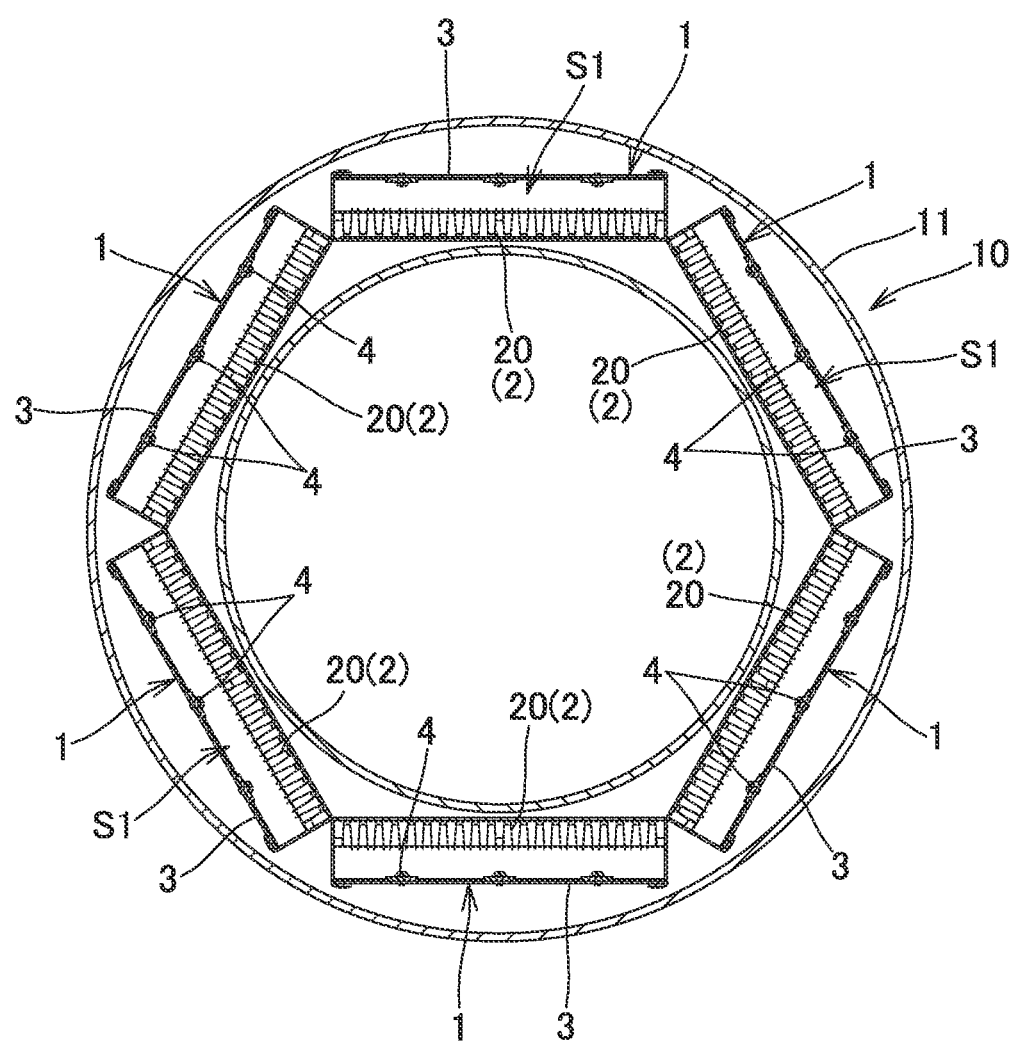
FIG. 14 is a longitudinal cross-sectional view of still another example of the fluid purifying apparatus.

FIG. 14 shows still another example of the air purifying apparatus 10. This example in which the units (photocatalytic devices 1) are arranged continuously in the circumferential direction in a cylindrical fluid flow path of the housing 11 is also preferable. Other than these structures, the air purifying apparatus 10 may have any structure in which fluid can pass through each unit. A fan for forcibly supplying fluid to each unit is preferably disposed in the fluid flow path of the housing 11.

Next, another embodiment (photocatalytic device 1A) of the photocatalytic device according to the present invention will be described with reference to FIG. 16 to FIG. 19.

The photocatalytic device 1A of the present embodiment incudes the photocatalyst filter 2, a housing 3A, and the light applying portions 4. The photocatalyst filter 2 includes the corrugated member 20 in which a plurality of the ridge portions 21 and a plurality of the trough portions 22 are respectively formed on the upper side and the lower side so that the ridge portions 21 and the trough portions 22 alternate. The housing 3A covers the upper and lower faces of the photocatalyst filter 2. The light applying portions 4 are disposed in the housing 3A on the inner face of the upper-side inner wall 32 that covers the upper face of the photocatalyst filter 2, and also on the inner face of a lower-side inner wall 33A that covers the lower face of the photocatalyst filter 2. The light applying portions 4 apply ultraviolet light or visible light toward the upper face or the lower face of the photocatalyst filter 2. The photocatalyst filter 2 is the same as that described above for the representative embodiment. However, in the present embodiment, the light passage holes 23 are formed in the bottom portions of the trough portions 22 without being omitted.

In the housing 3A of the present embodiment, the lower-side inner wall 33A is not a flat-plate-like wall but a wall that has a substantially open-ended triangular cross-sectional shape and includes tilted portions 332, 334 and a center portion 333, similarly to the upper-side inner wall 32. That is, in the lower-side inner wall 33A, both end portions 331, 335 in the lateral direction D1 are in contact with the lower faces of both end portions, in the same direction, of the photocatalyst filter 2 to support the photocatalyst filter 2, and form the lower-side edge portions 31 for the openings 3a, 3b, and the center portion 333 in the lateral direction D1 is positioned so as to be distant from the lower face of the center portion, in the same direction, of the photocatalyst filter 2 over a predetermined distance H1 in the downward direction, and the light applying portion 4 is disposed on the upper face side of the center portion 333.

Figure 19:
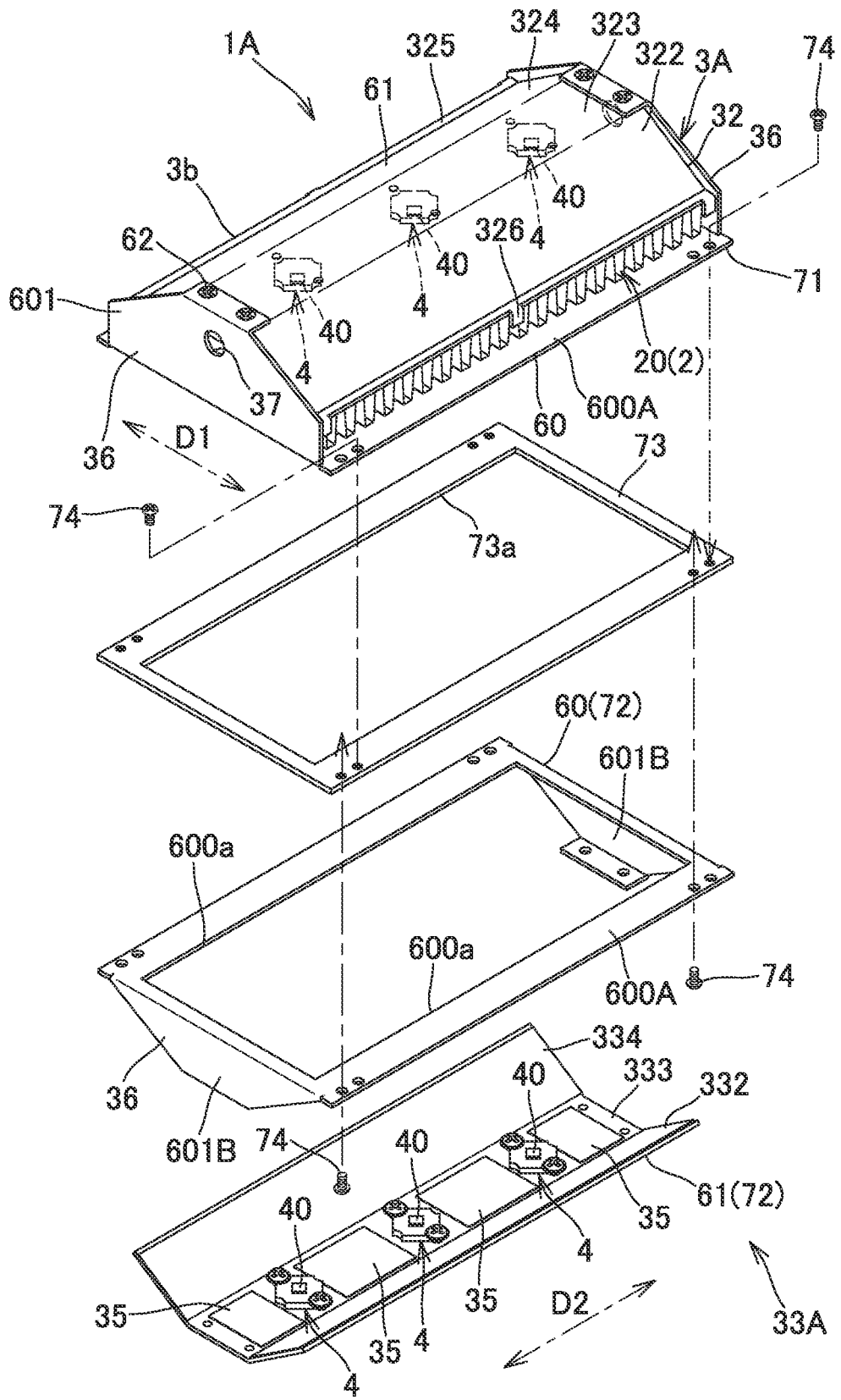
FIG. 19 is an exploded perspective view of the photocatalytic device.

As shown in FIG. 19, in the light applying portion 4, a plurality of the light sources 40 are disposed, on the upper face side of the center portion 333 of the lower-side inner wall 33A, at predetermined intervals in the direction D2 which is the longitudinal direction orthogonal to the lateral direction D1 and in which the ridge portions and the trough portions are aligned. Ina region, of the upper face of the center portion 333, other than a portion in which the light applying portions 4 are disposed, the reflective surface 35 is formed to reflect again light reflected by and returned from the photocatalyst filter 2 toward the photocatalyst filter 2.

The tilted portions 332, 334 are positioned in regions between both the end portions 331, 335 and the center portion 333. A distance in the downward direction between each of the tilted portions 332, 334 and the lower face of the photocatalyst filter 2 is gradually increased from both the end portions 331/335 side toward the center portion 333. Thus, a substantially trapezoidal-prism-shaped extra space S2 is formed between the lower-side inner wall 33A and the photocatalyst filter 2. Fluid flowing through the inflow port (opening 3a) into the housing 3A moves in the photocatalyst filter 2 (between the ridge portions and the trough portions) along the lateral direction D1, moves toward the upper space S1 and the lower space S2 while generating vortexes, returns into the photocatalyst filter 2, and flows through the outflow port (opening 3b) to the outside of the housing.

Thus, a distance over which and a time during which fluid and the photocatalyst layer on the surface of the photocatalyst filter 2 are in contact with each other can be increased, thereby enhancing the purification effect. Simultaneously, fluid having moved into each of the spaces S1, S2 comes into contact with the lower face of the upper-side inner wall 32 (the tilted portions 322, 324, the center portion 323) and the upper face of the lower-side inner wall 33A (the tilted portions 332, 334, the center portion 333), and heat emitted from the light applying portion 4 is efficiently dissipated into the fluid through the upper-side inner wall 32 and the lower-side inner wall 33A (as heat sinks).

Heat from the light applying portions 4 on each of the upper-side inner wall 32 and the lower-side inner wall 33A is transmitted also to both the end portions 321, 325 of the upper-side inner wall 32 and both the end portions 331, 335 of the lower-side inner wall 33A. The heat is dissipated into the fluid and is also transmitted to the photocatalyst filter 2 formed of a metal. Thus, the heat is efficiently exhausted into the fluid from the surface of the photocatalyst filter 2. Thus, according to the present embodiment, the upper-side inner wall 32 and the lower-side inner wall 33A of the housing 3A, and the photocatalyst filter 2 can be caused to efficiently function as a heat sink.

Similarly to the upper-side inner wall 32, the reflective surfaces 34 that reflect light are formed on the upper faces of the tilted portions 332, 334 of the lower-side inner wall 33A. Thus, light emitted from the light applying portion 4 is efficiently reflected toward the photocatalyst filter 2, and light reflected by and returned from the photocatalyst filter 2, or light, from the upper-side inner wall 32 side, which has passed through the photocatalyst filter 2 is reflected again toward the photocatalyst filter 2. In the present embodiment, the reflective surface 34 of the upper-side inner wall 32 also reflects again light, from the lower-side inner wall 33A side, which has passed through the photocatalyst filter 2, toward the photocatalyst filter 2.

Also in the present embodiment, the interior of the housing 3A is substantially enclosed except for the wiring hole 37 and the fluid inflow port and the fluid outflow port (openings 3a, 3h), and fluid having moved into the space St or the space S2 is returned toward the photocatalyst filter 2 and flows out while being purified by catalytic action.

The housing 3A of the present embodiment includes two divisional housings including upper and lower divisional housings 71, 72 that form internal spaces communicating with each other, and a loop-shaped connecting plate 73 connecting the housings 71 and 72. The first upper-side divisional housing 71 includes a base plate 600A having an opening 600a formed by cutting the base plate 600 of the housing 3 of the representative embodiment to form the center portion having almost the same shape as the upper and the lower faces of the photocatalyst filter 2 (shape set to be smaller by a predetermined dimension so as to lock the edge portion of the lower face of the photocatalyst filter 2). The photocatalyst filter 2 is accommodated inside the first divisional housing 71.

The second lower-side divisional housing 72 includes trapezoidal side plates 601B each formed by omitting a region corresponding to the end portions of the photocatalyst filter from the side plates of the first divisional housing, and other portions of the second divisional housing 72 have the same structure as those of the first divisional housing 71. The divisional housings 71, 72 are vertically unified via the connecting plate 73 by fixing the base plates 600A to the connecting plate 73 by mounting screws 74.

The connecting plate 73 is a loop-shaped plate member as described above, has thereinside an opening 73a having almost the same shape and size as the opening 600a of the base plate 600A, and is joined to the base plates 600A such that the openings 600a, 73a overlap each other at the same positions. The spaces S1 and S2 communicate with each other via the openings 600a and 73a. In the present embodiment, in such a structure, the base plates 600A of the upper and the lower housings and the connecting plate 73 form the lower-side edge portion 31 described above. However, the housing 3A of the present embodiment is not limited to such a structure in any way.

The other components, the modification, usability of a plurality of the photocatalytic devices incorporated as units into the housing of the air purifying apparatus, and the like are the same as those described for the representative embodiment with reference to FIG. 1 to FIG. 15. Therefore, the same components are denoted by the same reference numerals, and the detailed description thereof is omitted.

Figure 20:
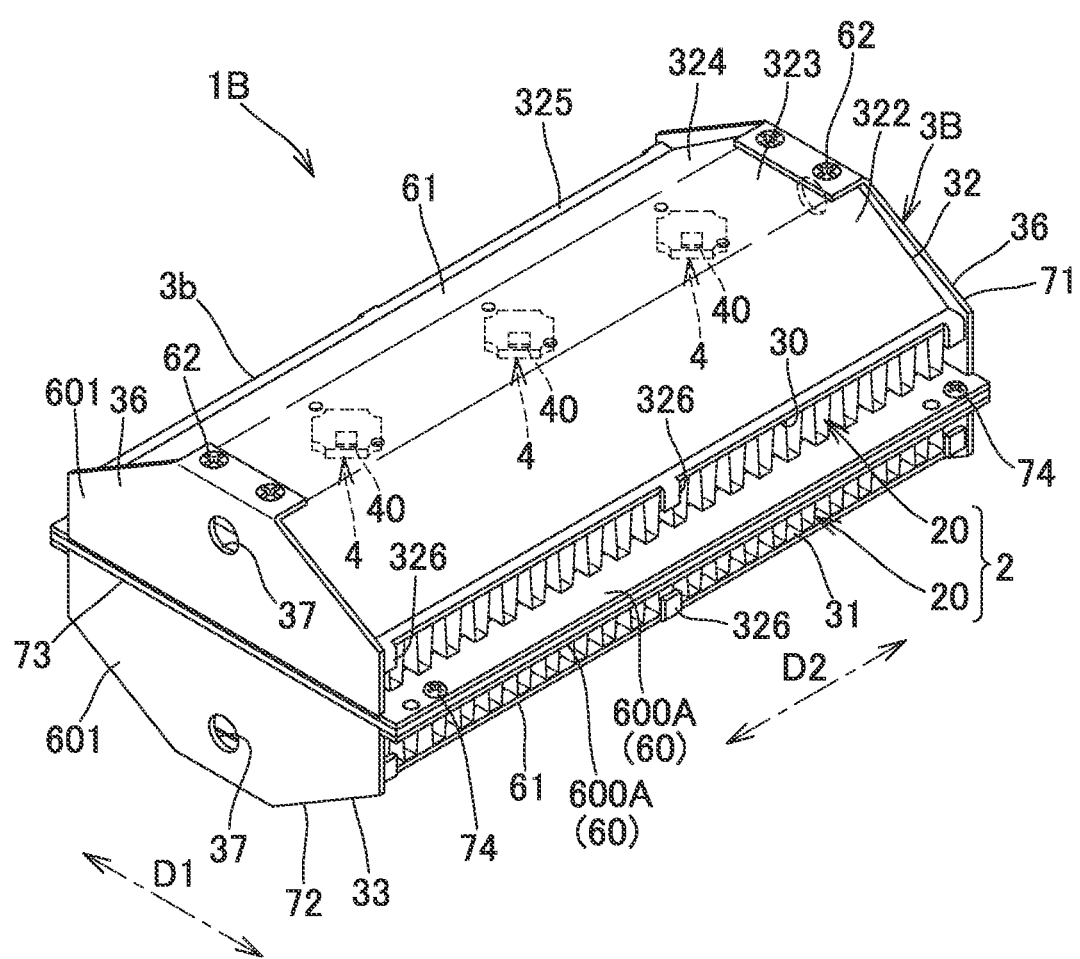
FIG. 20 is a perspective view of a photocatalytic device according to still another embodiment of the present invention.
Figure 21:
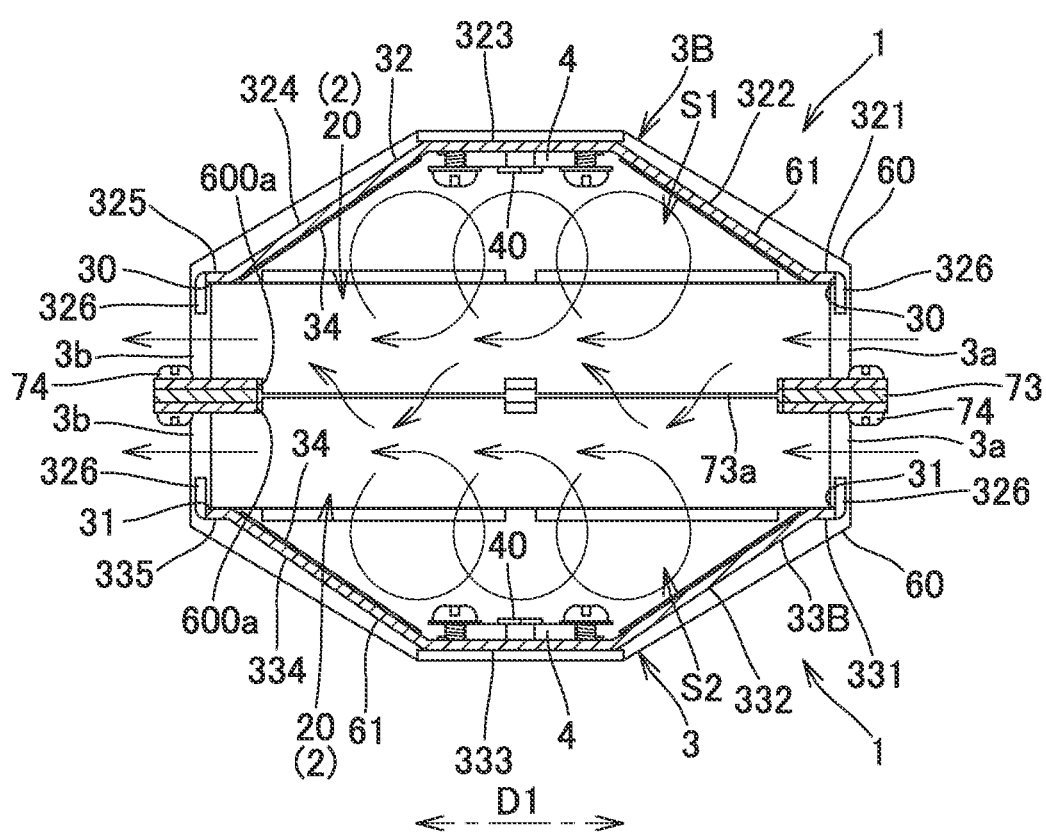
FIG. 21 is a transverse cross-sectional view of the photocatalytic device.
Figure 22:
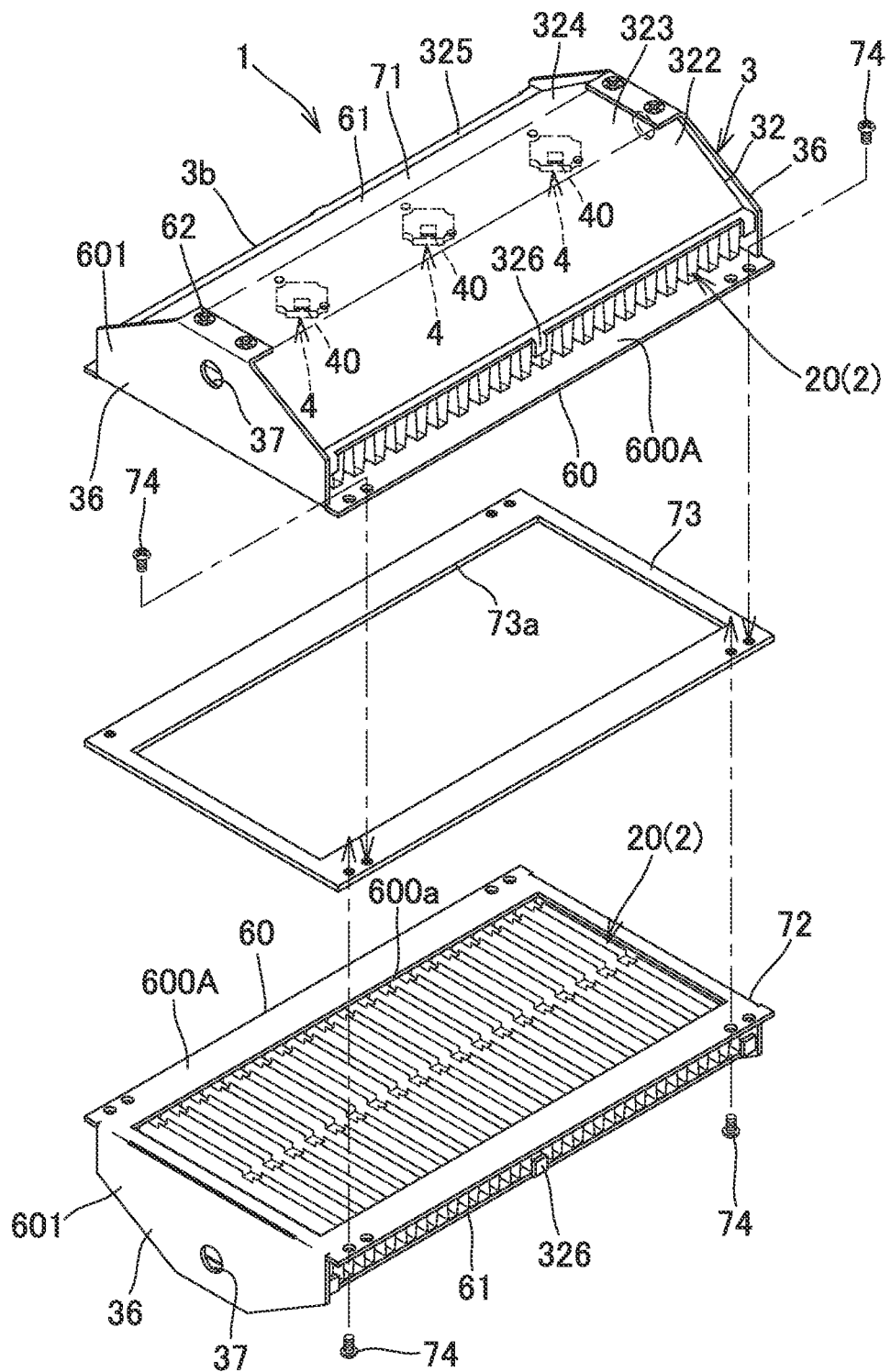
FIG. 22 is an exploded perspective view of the photocatalytic device.

Next, still another embodiment (photocatalytic device 1B) of the photocatalytic device according to the present invention will be described with reference to FIG. 20 to FIG. 22.

The photocatalytic device 1B of the present embodiment has a structure in which two corrugated members 20 each having a plurality of the ridge portions 21 and a plurality of the trough portions 22 respectively formed on the upper side and the lower side so that the ridge portions 2.1 and the trough portions 22 alternate, are continuously disposed so as to be parallel to each other in the upper and lower side to form the photocatalyst filter 2 in the photocatalytic device 1A of another embodiment described above. Each of the corrugated members 20 of the photocatalyst filter 2 has the light passage holes 23 at the bottom portions of the trough portions 22 without being omitted, similarly to the corrugated member 20 of the photocatalytic device 1A. Similarly to the housing 3A of the photocatalytic device 1A, a housing 3B includes the upper-side inner wall 32 and the lower-side inner wall 33B each having a substantially open-ended triangular cross-sectional shape, and a substantially trapezoidal-prism-shaped extra space S1 is formed between the upper-side inner wall 32 and the upper face of the corrugated member 20 on the upper side of the photocatalyst filter 2, and a substantially trapezoidal-prism-shaped extra space S2 is formed between the lower-side inner wall 33B and the lower face of the corrugated member 20 on the lower side of the photocatalyst filter 2.

The light applying portions 4 are similarly disposed at the center portions 323 and 333 of the upper-side and the lower-side inner walls 32 and 33B, respectively. Fluid flowing through the inflow port opening 3a) into the housing 3B moves in the upper and the lower corrugated members 20 (between the ridge portions and the trough portions) that form the photocatalyst filter 2, along the lateral direction D1, moves toward the upper space S i and the lower space S2 while generating vortexes, returns into the corrugated members 20, and flows through the outflow port (opening 3b) to the outside of the housing.

In the photocatalytic device 1B having such a structure, the volume of the photocatalyst filter is twice greater than that of the photocatalytic device 1A described above. Therefore, the purification effect can be further augmented, and heat emitted from the light applying portion 4 can be more efficiently dissipated into fluid from the surface of the photocatalyst filter 2 itself. In the present embodiment, two corrugated members 20 are arranged in the upper side and the lower side. However, it will be understood that three or more corrugated members 20 may be disposed.

The housing 3B of the present embodiment includes two divisional housings including upper and lower divisional housings 71, 72 that form internal spaces communicating with each other, and the loop-shaped connecting plate 73 between the housings 71 and 72, similarly to the housing 3A of the photocatalytic device 1A described above. However, the housing 3B is different from the housing 3A in that the lower-side divisional housing 72 and the upper-side divisional housing 71 have the same structure to accommodate the corrugated members 20 in the housing 3B. Thus, the upper and the lower divisional housings can use components common to each other, so that cost can be reduced.

The other components, the modification, usability of a plurality of the photocatalytic devices incorporated as units into the housing of the air purifying apparatuses, and the like are the same as those described for the representative embodiment with reference to FIG. 1 to FIG. 15 and another embodiment (photocatalytic device 1A) with reference to FIG. 16 to FIG. 19. Therefore, the same components are denoted by the same reference numerals, and the detailed description thereof is omitted.

While the present invention has been described based on the embodiments, the present invention is not limited to the embodiments in any way. It will be understood that numerous modifications and variations can be devised without departing from the gist of the present invention.

REFERENCE SIGNS LIST 1, 1A, 1B Photocatalytic device
2 Photocatalyst filter
3, 3A, 3B Housing
3a, 3b Opening
4 Light applying portion
5 Heat absorbing block
10 Air purifying apparatus
11 Housing
20 Corrugated member
21 Ridge portion
22 Trough portion
23 Light passage hole
24 Standing piece
25 Bridge portion
30 Upper-side edge portion
31 Lower-side edge portion
32 Upper-side inner wall
33, 33A Lower-side inner wall
34 Reflective surface
35 Reflective surface
36 Side wall
40 Light source
60 Base portion
61 Lid portion
62 Mounting screw
71, 72 Divisional housing
73 Connecting plate
73a Opening
74 Mounting screws
321, 325 End portion
322, 324 Tilted portion
323 Center portion
326 Locking piece
330 Reflective surface
331, 335 End portion
332 Tilted portion
333 Center portion
600, 600A Base plate
600a Opening
601, 601B Side plate
D1 Lateral direction D2 Longitudinal direction
H1 Distance
H2 Distance
S1, S2 Space

What is claimed is:

1. A photocatalytic device comprising:
a photocatalyst filter including a corrugated member in which a plurality of ridge portions and a plurality of trough portions are respectively formed on an upper side and a lower side of the corrugated member so that each of the ridge portions and each of the trough portions alternate, the photocatalyst filter having, at a top portion of each of the ridge portions, a light passage hole penetrating through the top portion of the ridge portion so that ultraviolet light or visible light passes through the light passage hole, the photocatalyst filter having, on a surface thereof, a photocatalyst carried, wherein the photocatalyst filter has an upper face extending at each of the opposing end portions, in the lateral direction, of the photocatalyst filter, and at a center portion, in the lateral direction, of the photocatalyst filter;
a housing configured to cover an upper side and a lower side of the surface of the photocatalyst filter, the housing having openings as a fluid inflow port or a fluid outflow port, at positions corresponding to opposite end portions of the ridge portions and the trough portions of the photocatalyst filter in a lateral direction along which the ridge portions and the trough portions of the photocatalyst filter extend; and
a light applying portion disposed on an upper-side inner wall of the housing which covers the upper face of the photocatalyst filter, the light applying portion being configured to apply ultraviolet light or visible light toward the upper face of the photocatalyst filter, wherein
the upper-side inner wall of the housing has opposite end portions in the lateral direction, which are in contact with upper faces located at opposite end portions, in the lateral direction, of the photocatalyst filter to support the photocatalyst filter, and the opposite end portions of the upper-side inner wall form upper-side edge portions for the openings,
the upper-side inner wall has a center portion in the late=ral direction, which is positioned with a predetermined distance upwardly from the upper face located at the center portion, in the lateral direction, of the photocatalyst filter,
tilted portions, each being positioned in regions between a respective one of the opposite end portions and the center portion of the upper-side inner wall so that a distance in the upward direction between each of the tilted portions and the upper face of the photocatalyst filter is gradually increased from the opposite end portion toward the center portion,
a lower-side inner wall of the housing covers a lower face of the photocatalyst filter, is in contact with the lower face of the photocatalyst filter to support the photocatalyst filter, and forms lower-side edge portions for the openings, and
the light applying portion is disposed on a lower face of the center portion of the upper-side inner wall.

2. The photocatalytic device according to claim 1, wherein reflective surfaces that reflect the light are formed on lower faces of the tilted portions of the upper-side inner wall.

3. The photocatalytic device according to claim 1, wherein a plurality of light sources are disposed, as the light applying portion, on the lower face of the center portion of the upper-side inner wall, at predetermined intervals in a longitudinal direction which is orthogonal to the lateral direction, the ridge portions and the trough portions being aligned in the longitudinal direction.

4. A fluid purifying apparatus comprising the photocatalytic device according to claim 1 incorporated as a unit, wherein fluid is caused to pass through a plurality of the units.

5. A fluid purifying apparatus comprising the photocatalytic device according to claim 2 incorporated as a unit, wherein fluid is caused to pass through a plurality of the units.

6. A fluid purifying apparatus comprising the photocatalytic device according to claim 3 incorporated as a unit, wherein fluid is caused to pass through a plurality of the units.

* * * * *